(12) United States Patent
Yang et al.

(10) Patent No.: US 6,726,931 B2
(45) Date of Patent: Apr. 27, 2004

(54) PROCESS FOR PREPARING ORAL SUSTAINED-RELEASE FORMULATION OF FELODIPINE

(75) Inventors: Yea-Sheng Yang, Hsin-Ying (TW); Ya-Ching Changchien, San-Min Dist. (TW)

(73) Assignee: Standard Chem. & Pharm. Co., Ltd., Hsin-Ying (TW)

( * ) Notice: Subject to any disclaimer, the term of this patent is extended or adjusted under 35 U.S.C. 154(b) by 57 days.

(21) Appl. No.: 10/118,690

(22) Filed: Apr. 8, 2002

(65) Prior Publication Data

US 2003/0190356 A1 Oct. 9, 2003

(51) Int. Cl.$^7$ .................................................. A61K 9/14
(52) U.S. Cl. ...................... 424/488; 424/480; 424/475; 424/486; 424/464; 424/451; 424/468
(58) Field of Search ................................. 424/464, 488, 424/480, 475, 486, 451, 456, 468

(56) References Cited

U.S. PATENT DOCUMENTS 4,803,081 A * 2/1989 Falk et al. .................. 424/488

\* cited by examiner

Primary Examiner—Thurman K. Page
Assistant Examiner—Rachel M. Bennett
(74) Attorney, Agent, or Firm—Dellett & Walters

(57) ABSTRACT

The present invention relates to a process for producing an oral sustained-release pharmaceutical composition of felodipine. The process includes mixing together felodipine with at least an ionic surfactant or hydrophilic polymer, and at least a release-controlling excipient. The pharmaceutical composition of felodipine produced by the process of the present invention possesses the enhanced dissolution rate of the insoluble drug of felodipine, whereas the sustained releasing profile and superior bioavailability of the produced pharmaceutical composition of felodipine are retained.

23 Claims, 2 Drawing Sheets

PROCESS FOR PREPARING ORAL SUSTAINED-RELEASE FORMULATION OF FELODIPINE

BACKGROUND OF THE INVENTION

1. Field of the Invention

The present invention relates to a process for preparing an oral formulation of felodipine, and more particularly to a process that manufactures the felodipine formation with sustained releasing efficiency.

2. Description of Related Art

Felodipine is a calcium blocker that efficiently promotes oxygen and blood supplement to the coronary artery and dilates the periphery of blood vessels. Therefore, felodipine is widely used in clinic for treating patients of coronary stenosis and hypertension. However, conventional felodipine formulations cannot be released over a period of more than a couple of hours so that patients have to take felodipine-containing medicaments frequently. If the patients forget to take felodipine or cannot do so during sleep, no sustained protective effects of felodipine are provided. Consequently, the patients confront a high risk of suffering from a heart attack.

There is an existed pharmaceutical preparation of sustained-release medicine, as described in U.S. Pat. No. 4,803,081. U.S. Pat. No. 4,803,081 disclosed an extended release preparation of an active compound, including felodipine, with very low solubility. The conventional preparation contains the active compound dissolved or dispersed in a semi-solid or liquid non-ionic solubilizer as well as a process for the preparation thereof. The process of U.S. Pat. No. 4,803,081 demands the use of the amount by weight of the solubilizer at least equal to the amount by weight of the active compound. It is noted that the solubilizer used according to U.S. Pat. No. 4,803,081 is a non-ionic surfactant, which causes an insufficient dissolubility to the inert-dissolving felodipine. Therefore, felodipine would not be well mixed with other ingredients contained inside the medicine, unless felodipine has to be dissolved in non-ionic surfactant (preferably polyoxyl 40 stearate) first and then mixed with a carrier material, such as HPMC, xanthan gum, guar gum and calcium phosphate. Inevitably, two steps for admixing are required according to U.S. Pat. No. 4,803,081.

There is still a need in this art of a more economical process for the manufacture of sustained release medicines including felodipine.

SUMMARY OF THE INVENTION

An objective of the present invention is to provide a process for preparing orally administered, sustained-release felodipine formulations by means of one-step mixing. The process according to the present invention comprising mixing felodipine together with at least an ionic surfactant or hydrophilic polymer and at least a release-controlling excipient to form a uniform felodipine mixture. The release-controlling excipient is selected from hydrophilic colloid, hydrophobic cellulose and wax.

Preferably, the ionic surfactant employeds according to the present invention includes sodium dioctylsulfonyl succinate or sodium lauryl sulfate.

Preferably, the hydrophilic polymer employed according to the present invention includes polyvinyl pyrrolidone (PVP), hydroxyethyl cellulose (HEC), hydroxy propyl cellulose (HPC), hydroxypropylmethyl cellulose (HPMC) or polyvinyl alcohol (PVA).

Preferably, the release-controlling excipient employed according to the present invention includes gelatin, shellac, hydroxypropylmethyl cellulose (HPMC), methylcellulose (MC), ethylcellulose (EC), hydroxypropylmethyl cellulose phthalate (HPMCP), cellulose phthalate acetate (APC), methacrylic acid/methyl methacrylate copolymers, polyvinyl acetate phthalate (PVAP), glyceryl behenate, paraffin or carnauba wax.

The process according to the present invention may further comprise mixing a diluent with the felodipine mixture. The diluent employed according to the present invention includes microcrystalline cellulose, starch, lactose, silicon dioxide, calcium biphosphate, calcium phosphate, calcium carbonate, magnesium carbonate, aluminum silicate, magnesium silicate or mannitol. Preferably, the diluent is microcrystalline cellulose, lactose, silicon dioxide or calcium biphosphate.

The process according to the present invention may further comprise mixing a lubricant with the felodipine mixture. Preferably, the lubricant employed according to the present invention is talc powder, stearic acid, stearyl acetate, sodium stearyl fumarate or glyceryl behenate.

The process according to the present invention may further comprise compressing the felodipine mixture into tablets.

The process according to the present invention may further comprise encapsulating the felodipine mixture.

The process according to the present invention may further comprise mixing the felodipine mixture with water or an organic solvent, and granulating the resultant mixture into granules by a conventional wet-granulation method. The organic solvent employed includes alcohol, acetone, isopropanol, dichloromethane or other dissolvable media. The process according to the present invention may further comprise drying the granules followed by compressing the dried granules into tablets or encapsulating the dried granules. In this respect, preferably, the process according to the present invention further comprises coating the tablets with a light-resisting film. More preferably, the light-resisting film is made of material selected form the group consisting of hydroxypropylmethyl cellulose, polyethylene glycol, titanium dioxide and ferrous oxide. In a preferred embodiment of the process according to the present invention, the granules are dried until a water-containing ratio of 0.4% to 6% (w/w) of the granules is attained.

Further benefits and advantages of the present invention will become apparent after reading the detailed description.

DETAILED DESCRIPTION OF THE INVENTION AND PREFERRED EMBODIMENTS

Figure 1:
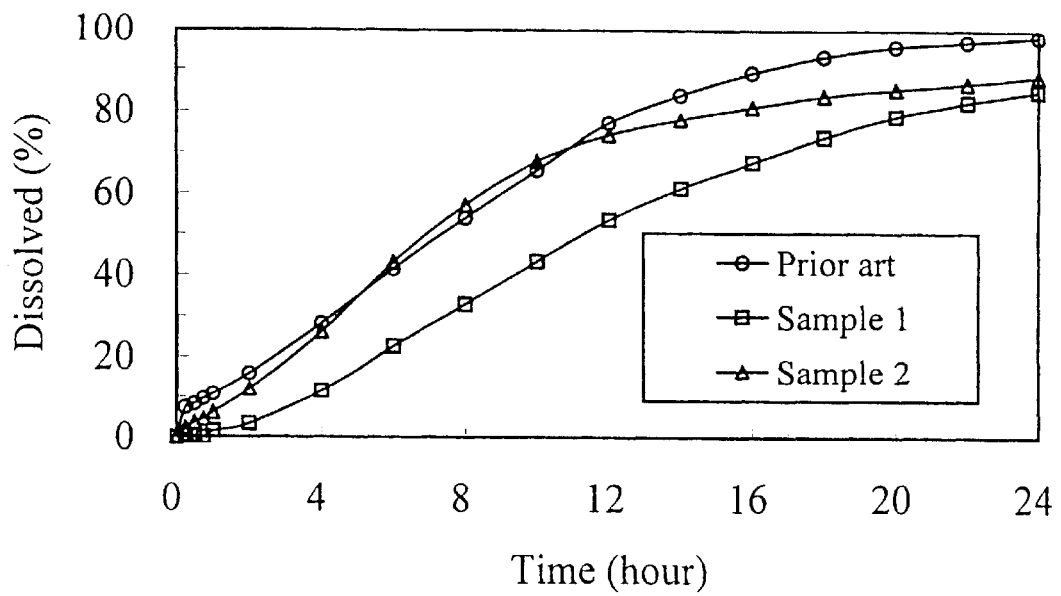
FIG. 1 is a graph of the active ingredient-dissolution rates of the oral felodipine formulation made with the process in accordance with the present invention and the prior art.

Detailed procedures of this invention are described in the following steps:

(1). Evenly mixing the felodipine with hydrophilic polymer or ionic surfactant and release-controlling excipients, wherein the release-controlling excipients are selected from hydrophilic colloid, hydrophobic cellulose or wax;

(2). Adding diluents such as microcrystalline cellulose, lactose, silicon dioxide into the mixture of step (1) if necessary;

(3). Further adding lubricants into the mixture and making the mixture of the felodipine into tablets or granules enclosed in capsules or adding water or organic solvents into the mixture and make the mixture of felodipine into granules. After drying the granules to 0.4%–6% water-containing ratio, adding lubricants into the granules and then compressing the mixture into tablets in spheroid or stuffing the granules into capsules. Moreover, the tablets are coated with a light-resisting film if necessary.

The ionic surfactants used in this invention include sodium dioctyl sulfonyl succinate or sodium lauryl sulfate.

The hydrophilic polymers used in this invention include polyvinyl pyrrolidone (PVP), hydroxyethyl cellulose (HEC), hydroxy propyl cellulose (HPC), hydroxypropylmethyl cellulose (HPMC) or polyvinyl alcohol (PVA).

The release-controlling excipients used in this invention include gelatin, shellac, hydroxypropylmethyl cellulose (HPMC), methylcellulose (MC), ethylcellulose (EC), hydroxypropylmethyl cellulose phthalate (HPMCP), acetate phthalate cellulose (APC), methacrylic acid/methacrylate copolymer, polyvinyl acetate phthalate (PVAP), glyceryl behenate, paraffin wax or carnauba wax.

The diluents used in this invention include microcrystalline cellulose, starch, lactose, silicon dioxide, calcium biphosphate, calcium phosphate, calcium carbonate, magnesium carbonate, aluminum silicate, magnesium silicate or glyceryl alcohol.

The solvents used in this invention include water, alcohol, acetone, isopropanol, dichloromethane or other dissolvable mediums.

The lubricants used in this invention include talc powder, stearic acid, stearic acetate, sodium stearyl fumarate or glyceryl behenate.

The light-resisting films are made of materials include hydroxypropylmethyl cellulose, polyethylene glycol, titanium dioxide, or ferrous oxide.

Preferably, the process of preparing sustained-released felodipion oral formulation further comprises that mixing the felodipine mixture with water or an organic solvent, and then granulating the resultant mixture into granules by a wet-granulation method, wherein the solvent is alcohol, acetone, isopropanol, dichloromethane or other dissolvable media. In a preferred embodiment of the present invention, the granules are dried until water-containing ratio of the granules is 0.4% to 6% (w/w) and then the dried granules are compressed into tablets or encapsulated into capsules. The tablets made are preferably coated with a light-resisting film, wherein the light-resisting film is made of materials including hydroxypropylmethyl cellulose, polyethylene glycol, titanium dioxide and ferrous oxide.

Following examples are provided to further explain the present invention. However, the scope of the present invention should not be limited by these examples.

EXAMPLE 1

Formulation:

| (1) felodipine | 1 g |
|---|---|
| hydroxypropylmethy cellulose | 72 g |
| glycery behenate | 15 g |

Procedure:

1 g of felodipine, 72 g of hydroxypropylmethyl cellulose and 15 g of glyceryl behenate were mixed together to prepare a felodipine mixture.

The felodipine mixture was compressed into tablets by a rotating tablet-making machine, wherein the tablets were round convex disks of 11.0 mm diameter and of 3–8 kg-f hardness.

EXAMPLE 2

Formulation:

| (1) felodipine | 1 g |
|---|---|
| hydroxypropylmethy cellulose | 44 g |
| glycery behenate | 24 g |
| lactose | 8 g |
| silicon dioxide | 11 g |

Procedure:

1 g of felodipine, 44 g of hydroxypropylmethyl cellulose, 24 g of glyceryl behenate, 8 g of lactose and 11 g of silicon dioxide were mixed together to prepare a felodipine mixture.

Then, the felodipine mixture was compressed into tablets by a rotating tablet-making machine, wherein the tablets were round convex disks of 11.0 mm diameter and of 3–8 kg-f hardness.

EXAMPLE 3

Formulation:

| (1) felodipine | 1 g |
|---|---|
| polyvinyl pyrrolidone(PVP) | 62 g |
| glycery behenate | 12 g |
| calcium biphosphate | 10 g |
| lactose | 3 g |

Procedure:

1 g of felodipine, 62 g of polyvinyl pyrrolidone (PVP), 12 g of glyceryl behenate, 10 g of calcium biophosphate and 3 g of lactose were mixed together to prepare a felodipine mixture.

The felodipine mixture was compressed into tablets by a rotating tablet-making machine, wherein the tablets were round disks of 11.0 mm diameter and of 3–8 kgf hardness.

EXAMPLE 4

Formulation:

| (1) felodipine | 1 g |
|---|---|
| sodium lauryl sulfate | 44 g |
| glycery behenate | 24 g |

-continued

| | |
|---|---|
| silicon dioxide | 1.6 g |
| lactose | 17 g |
| (2) water | proper quantity |
| (3) magnesium stearate | 0.4 g |

Procedure:

1 g of felodipine, 44 g of sodium lauryl sulfate, 24 g of glyceryl behenate, 1.6 g of silicon dioxide, and 17 g of lactose were mixed together to prepare a felodipine mixture.

The felodipine mixture was mixed with water of proper quantity to refine into wet granules. The wet granules were dried at 50° C. until the water-containing ratio reached 0.4~6% (w/w). After drying, the wet granules were evenly mixed with 0.4 g of magnesium stearate and then enclosed in capsules.

EXAMPLE 5

Formulation:

| | |
|---|---|
| (1) felodipine | 1 g |
| sodium lauryl sulfate | 1 g |
| hydroxypropylmethyl cellulose | 48 g |
| microcrystalline cellulose | 2 g |
| silicon dioxide | 30 g |
| lactose | 4 g |
| (2) alcohol | proper quantity |
| (3) sodium stearyl fumarate | 2 g |
| (4) hydroxypropylmethyl cellulose | 4.39 g |
| polyethylene alcohol | 0.79 g |
| titanium dioxide | 0.21 g |
| purified water | proper quantity |
| 95% alcohol | proper quantity |

Procedure:

1 g of felodipine, 1 g of sodium lauryl sulfate, 48 g of hydroxypropylmethyl cellulose, 2 g of microcrystalline cellulose, 30 g of silicon dioxide and 4 g of lactose were mixed together to prepare a felodipine mixture.

Then, felodipine mixture was mixed alcohol of proper quantity to refine into wet granules. The wet granules were dried at 45° C. until the water-containing ratio reached 0.4~6% (w/w). After drying, the wet granules were evenly mixed with 2 g of sodium stearyl fumarate and then compressed into tablets by a rotating tablet-making machine, wherein the tablets are round convex disks of 11.0 mm diameter and of 3–8 kg-f hardness. Lastly, the tablets were coated with a film made of (4) 4.39 g of hydroxypropylmethyl cellulose, 0.79 g of polyethylene alcohol, 0.21 g of titanium dioxide and 0.01 g of ferrous oxide.

EXAMPLE 6

Formulation:

| | |
|---|---|
| (1) felodipine | 1 g |
| microcrystalline cellulose | 24 g |
| silicon dioxide | 30 g |
| lactose | 3 g |
| glycery behenate | 30 g |

Procedure:

1 g of felodipine, 24 g of microcrystalline cellulose, 30 g of silicon dioxide, 3 g of lactose and 30 g of glyceryl behenate were mixed together to prepare a felodipine mixture.

The felodipine mixture was compressed into tablets by a rotating tablet-making machine, wherein the tablets were round convex disks of 11.0 mm diameter and of 3–8 kg-f hardness. This solubilizer-absent formulation was taken as a control group.

In vitro Dissolution Tests:

(a) Testing of Ingredient-Releasing Rates of the Felodipine Medicine:

The samples of felodipine medicine made accordingly to examples 1–6 and market-available felodipine medicine (i.e. prior art in the figures) were tested for ingredient-releasing rates by a dissolution test under principles of U.S.P. (United States pharmacopoeia) $24^{th}$ edition. In this testing, the felodipine medicines and 900 ml of 0.1N hydrochloric acid (containing 0.1% oleic polyalcohol sorbitan ester) were poured into a testing vessels and heated up to 37±0.5° C. Then, the mixture was paddled in a mixer at 50 rpm.

Figure 2:
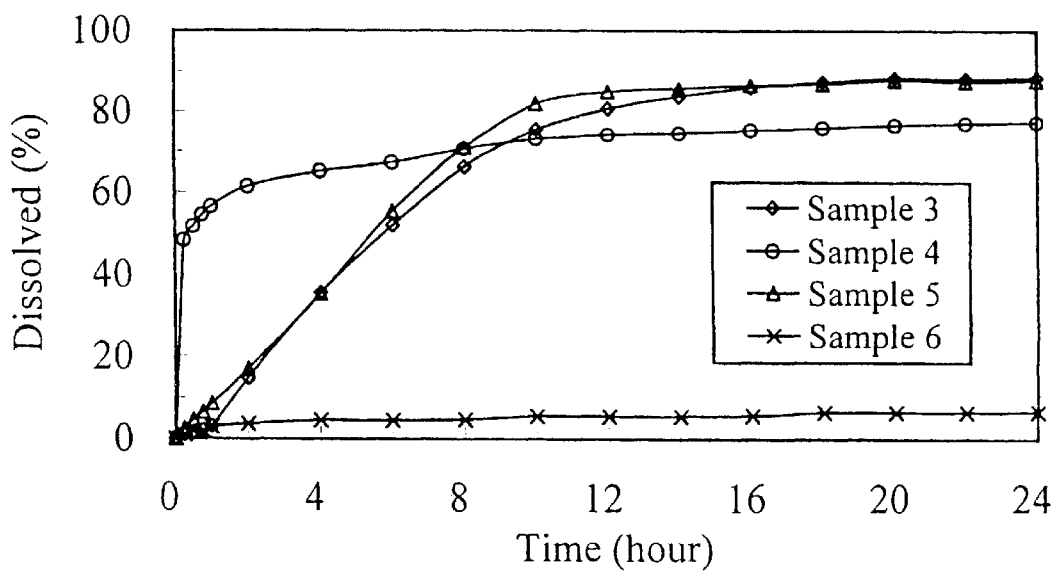
FIG. 2 is a graph of the active ingredient-releasing rates of the oral felodipine formulation made with other embodiments of the process in accordance with the present invention.

The results are shown in Table 1, FIGS. 1 and 2.

TABLE 1 active ingredient-releasing ratio (%) of the felodipine medicines in 0.1 N hydrochloric acid solution.

| Time (hrs) | Market-available | Example 1 | Example 2 | Example 3 | Example 4 | Example 5 | Example 6 |
|---|---|---|---|---|---|---|---|
| 0 | 0 | 0 | 0 | 0 | 0 | 0 | 0 |
| 0.25 | 7.31 | 0.20 | 2.32 | 0.98 | 48.39 | 2.53 | 0.94 |
| 0.50 | 8.24 | 0.20 | 3.68 | 1.57 | 51.69 | 4.62 | 1.76 |
| 0.75 | 9.60 | 0.00 | 4.59 | 2.16 | 54.55 | 6.52 | 1.76 |
| 1 | 10.69 | 1.38 | 6.01 | 2.95 | 56.55 | 8.47 | 2.85 |
| 2 | 15.93 | 3.36 | 11.97 | 14.74 | 61.31 | 16.96 | 3.58 |
| 4 | 28.08 | 11.45 | 26.05 | 35.56 | 64.93 | 35.26 | 4.43 |
| 6 | 41.40 | 22.51 | 42.98 | 51.86 | 67.10 | 55.38 | 4.43 |
| 8 | 53.83 | 32.79 | 57.06 | 66.01 | 70.51 | 70.81 | 4.66 |
| 10 | 65.78 | 43.26 | 68.02 | 75.45 | 73.09 | 81.91 | 5.51 |
| 12 | 77.29 | 53.52 | 74.42 | 80.76 | 74.24 | 84.93 | 5.51 |
| 14 | 84.13 | 61.42 | 78.21 | 83.71 | 74.66 | 85.76 | 5.51 |
| 16 | 89.45 | 67.93 | 81.26 | 86.07 | 75.51 | 86.63 | 5.75 |
| 18 | 93.36 | 74.05 | 83.99 | 87.64 | 76.08 | 87.02 | 6.60 |
| 20 | 95.88 | 79.18 | 85.65 | 88.62 | 76.79 | 87.98 | 6.60 |

TABLE 1-continued active ingredient-releasing ratio (%) of the felodipine medicines in 0.1 N hydrochloric acid solution.

| Time (hrs) | Market-available | Example 1 | Example 2 | Example 3 | Example 4 | Example 5 | Example 6 |
|---|---|---|---|---|---|---|---|
| 22 | 97.14 | 82.54 | 87.05 | 88.43 | 77.21 | 87.65 | 6.60 |
| 24 | 98.34 | 85.30 | 88.84 | 88.82 | 77.64 | 87.99 | 6.83 |

According to Table 1 in view of FIGS. 1 and 2, all felodipine medicines have the same quantity of felodipine composition, including the market-available felodipine medicine. The active ingredient-releasing ratios are maintained above 75% for 20 hours. However, example 6 which is the comparison medicine in this invention has only 6.6% active ingredient-releasing ratio much less than other samples that means the invention product of felodipine medicines could increase the releasing rate of very low water-soluble felodipine and show prolonged and nearly constant rate of drug release for a long period of time.

(b) human testing:

10 mg samples of felodipine medicines of example 5 and of market-available product were tested for concentration variation in human blood. The results were shown in Table 2 and FIG. 3.

TABLE 2

Concentration of felodipine medicines in human blood.

| Time (hrs) | Market-available | Example 5 |
|---|---|---|
| 0 | 0 | 0 |
| 0.5 | 1.03 | 0.553 |
| 1.0 | 2.02 | 2.54 |
| 1.5 | 3.62 | 3.46 |
| 2.0 | 4.16 | 4.38 |
| 2.5 | 4.09 | 4.17 |
| 3.0 | 4.21 | 3.74 |
| 3.5 | 3.88 | 3.51 |
| 4.0 | 3.28 | 3.22 |
| 5.0 | 3.20 | 2.84 |
| 6.0 | 2.45 | 2.23 |
| 8.0 | 1.57 | 1.57 |
| 10.0 | 1.30 | 1.23 |
| 12.0 | 0.920 | 1.12 |
| 24.0 | 0.341 | 0.579 |

Figure 3:
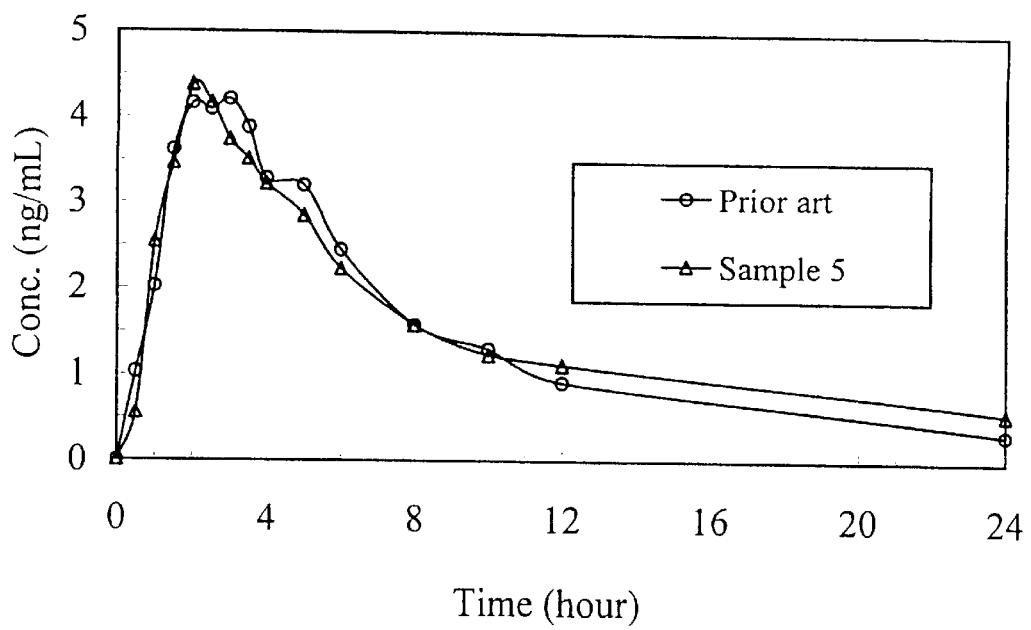
FIG. 3 is a graph of the active ingredient-releasing rates of the oral felodipine formulation made by the process in example 5 in accordance with the present invention and the prior art.

According to Table 2 and FIG. 3, both samples keep releasing felodipine composition into human blood for more than 24 hours. However, the sample in example 5 has less concentration variation than the sample of market-available product because the curve of example 5 is smoother than the one of market-available product.

Therefore, it is easily understood that the present invention has the following advantages:

1. In the present invention, the ionic-surfactant and hydrophilic polymer increase the dissolving efficiency of the felodipine drug, therefore, only one step is needed in this invention to mixing with other ingredient such as binder or carrier material and the process of preparing sustained-release felodipine formulation is shorten.
2. The felodipine drugs in the present invention have prolonged ingredient-releasing efficiency so that patients can reduce the frequency of taking felodipine medicine.
3. The concentration variations of the present invention in human blood is less than market-available product so that the felodipine drug in this invention is steady for releasing felodipine composition and is safer than the market-available product for the patients.

Various modifications and variations of the present invention will be recognized by those persons skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention, which are obvious to those skilled in the art, are intended to be within the scope of the following claims.

What is claimed is:

1. A process for preparing an oral sustained-release formulation of felodipine, comprising mixing felodipine, at least an ionic surfactant or hydrophilic polymer and at least a release-controlling excipient to form a uniform felodipine mixture in one step, wherein the release-controlling excipient is selected from hydrophilic colloid, hydrophobic cellulose and wax.

2. The process as claimed in claim 1, comprising mixing felodipine with at least an ionic surfactant and at least a release controlling excipient to form a uniform mixture in one step.

3. The process as claimed in claim 2, wherein the ionic surfactant is sodium dioctylsulfonyl succinate or sodium lauryl sulfate.

4. The process as claimed in claim 1, wherein the hydrophilic polymer is polyvinyl pyrrolidone (Pvp), hydroxyethyl cellulose (HEC), hydroxy propyl cellulose (HPC), hydroxypropylmethyl cellulose (HPMC) or polyvinyl alcohol (PVA).

5. The process as claimed in claim 1, wherein the release controlling excipient is gelatin, shellac, hydroxypropylmethyl cellulose (HPMC), methylcellulose (MC), ethylcellulose (EC), hydroxypropylmethyl cellulose phthalate (HPMCP), cellulose phthalate acetate (APC), methacrylic acid/methyl methacrylate copolymers, polyvinyl acetate phthalate (PVAP), glyceryl behenate, paraffin or carnauba wax.

6. The process as claimed in claim 1, which further comprises further adding a diluent in the step to form the felodipine mixture.

7. The process as claimed in claim 6, wherein the diluent is microcrystalline cellulose, starch, lactose, silicon dioxide, calcium biphosphate, calcium phosphate, calcium carbonate, magnesium carbonate, aluminum silicate, magnesium silicate or mannitol.

8. The process as claimed in claim 6, wherein the diluent is microcrystalline cellulose, lactose, silicon dioxide or calcium biphosphate.

9. The process as claimed in claim 6, which further comprises adding a lubricant in the step to form the felodipine mixture.

10. The process as claimed in claim 9, wherein the lubricant is talc powder, stearic acid, stearyl acetate, sodium stearyl fumarate or glyceryl behenate.

11. The process as claimed in claim 1, which further comprises compressing the felodipine mixture into tablets.

12. The process as claimed in claim 6, which further comprises compressing the felodipine mixture into tablets.

13. The process as claimed in claim 9, which further comprises compressing the felodipine mixture into tablets.

14. The process as claimed in claim 1, which further comprises encapsulating the felodipine mixture.

15. The process as claimed in claim 6, which further comprises encapsulating the felodipine mixture.

16. The process as claimed in claim 9, which further comprises encapsulating the felodipine mixture.

17. The process as claimed in claim 1, which further comprises:

mixing the felodipine mixture with water or an organic solvent, and granulating the resultant mixture into granules by a wet-granulation method.

18. The process as claimed in claim 17, which further comprises drying the granules followed by compressing the dried granules into tablets.

19. The process as claimed in claim 17, which further comprises drying the granules followed by encapsulating the dried granules.

20. The process as claimed in claim 18, which further comprising coating the tablets with a light-resisting film.

21. The process as claimed in claim 17, wherein the solvent is alcohol, acetone, isopropanol, dichloromethane or other dissolvable media.

22. The process as claimed in claim 20, wherein the light resisting film is made of material selected from the group consisting of hydroxypropylmethyl cellulose, polyethylene glycol, titanium dioxide and ferrous oxide.

23. The process as claimed in claim 17, wherein the granules are dried until a water-containing ratio of 0.4% to 6% (w/w) of the granules is attained.

* * * * *